United States Patent [19]

Andrews et al.

[11] Patent Number: 5,545,220
[45] Date of Patent: Aug. 13, 1996

[54] IMPLANTABLE PROSTHESIS WITH OPEN CELL TEXTURED SURFACE AND METHOD FOR FORMING SAME

[75] Inventors: Winston A. Andrews, Danville; David Nelson, San Jose; Richard W. Novy, Sunnyvale, all of Calif.

[73] Assignee: Lipomatrix Incorporated, Palo Alto, Calif.

[21] Appl. No.: 147,737

[22] Filed: Nov. 4, 1993

[51] Int. Cl.⁶ .................................................. A61F 2/02
[52] U.S. Cl. ........................... 623/11; 623/66; 623/16; 427/2.24; 427/202; 427/224; 427/264
[58] Field of Search ........................... 623/7, 8, 11, 12, 623/16, 66; 427/2.24, 202, 205, 224, 245, 264, 387, 412.1

[56] References Cited

U.S. PATENT DOCUMENTS

| | | | |
|---|---|---|---|
| 4,531,244 | 7/1985 | Hamas | 623/8 |
| 4,610,692 | 9/1986 | Eitenmuller et al. | 623/66 |
| 4,648,880 | 3/1987 | Brauman | 623/8 |
| 4,834,747 | 5/1989 | Gogolewski | 427/2.24 |
| 4,889,744 | 12/1989 | Quaid | 623/8 |
| 4,955,907 | 9/1990 | Ledergerber | 623/8 |
| 4,955,909 | 9/1990 | Ersek et al. | 623/8 |
| 4,960,425 | 10/1990 | Yan et al. | 623/8 |
| 4,963,150 | 10/1990 | Brauman | 623/8 |
| 5,007,929 | 4/1991 | Quaid | 623/8 |
| 5,011,494 | 4/1991 | von Recum et al. | 623/8 |
| 5,022,942 | 6/1991 | Yan et al. | 623/8 |
| 5,092,348 | 3/1992 | Dubrul et al. | 623/8 |
| 5,184,610 | 2/1993 | Marten et al. | 623/9 |
| 5,236,453 | 8/1993 | Picha | 623/8 |

*Primary Examiner*—Randy C. Shay
*Attorney, Agent, or Firm*—Howell & Haferkamp, L.C.

[57] ABSTRACT

A method for forming an open cell texturized surface in a silicone elastomer layer of a breast implant, or other medical implant, is created by forming a layer of uncured silicone elastomer, applying a coating of particles to the surface thereof, and curing the layer by heating it at an elevated temperature which also volatilizes the particles such that their constituent gases boil through the surface of the layer and create the texturing.

27 Claims, 3 Drawing Sheets

IMPLANTABLE PROSTHESIS WITH OPEN CELL TEXTURED SURFACE AND METHOD FOR FORMING SAME

BACKGROUND AND SUMMARY OF THE INVENTION

There has been much concern in the prior art with the external surfaces of medically implantable prostheses, including breast implants. One such concern with these implantable prostheses is the natural tendency for the human body to surround an implanted foreign substance with fibrous tissue to thereby isolate them from surrounding normal tissues. This encapsulation, called capsular contracture when involving mammary prostheses, is not desirable as there is a tendency for the scar tissue or capsule to contract. Ultimately, the capsule has been found to contract to assume a nearly spherical shape thereby detracting from the desired aesthetic appearance of a human breast. Furthermore, this can cause discomfort and may require correction through a surgical procedure which is not desired.

In the prior art, some attention has been paid to this problem and one of the approaches to partially solving this problem has been to texture the external surface of these implants. Various kinds of texturing have been tried in the prior art including open cell structure texturing as disclosed in U.S. Pat. Nos. 4,889,744 and 5,007,929, the disclosures of which are incorporated herein by reference. As described therein, a method may be used as a silicone elastomer surface is formed to create an open cell structure in the external surface thereof. This method generally comprises the steps of partially curing the external surface, applying a layer of solid particles to the surface before the layer is fully cured, fully curing the layer, and then dissolving the solid particles from the surface by dipping the surface into a solvent. The solvent must be chosen so as to dissolve only the solid particles and not affect the silicone elastomer surface. One example given is crystalline sodium chloride (salt) for the particles and water as the solvent. As disclosed therein, the method requires fully curing the layer with the solid particles being intact within the layer prior to dipping the layer into the solvent. However, the inventors believe that, in actual practice, the implant is first scrubbed with a stiff brush to perforate the encapsulated salt to speed up the dissolving process.

This prior art method is successful in forming a textured surface, but the texturing is limited by the nature of the method itself. First of all, the solid particles must be on the edge of the surface, or so closely adjacent as to be touching particles which are on the edge of the surface so that the solvent may reach the particles and dissolve them. As can be appreciated, water has no affect upon an elastomer so that any particles which are not so oriented will not be reached by the water as the water does not penetrate the silicone elastomeric material. Thus, the texturing is shallow and does not penetrate to any appreciable extent the surface of the layer. Furthermore, there is no interaction between the particles and the silicone elastomer as the particles are dissolved by the solvent. This is because the silicone elastomer has been fixed in shape in the curing step and the step of dissolving the particles takes place after the curing step. Again, this tends to limit the "roughness" of the surface whose shape is determined as the elastomer is cured and prior to the dissolving step. Thus, while there is some texturing achieved with the prior art method, it is limited in depth and "roughness".

In order to improve upon this prior art method of texturing silicone elastomeric surfaces which cover medically implantable prostheses and other devices, the inventors herein have succeeded in developing a method which not only increases the depth of the texturing and the "roughness" of the texturing, it also eliminates a separate dissolving step for the solid particles. Thus, not only is the surface better "texturized", so that it should experience greater physiological compatibility by optimizing tissue ingrowth with blood vessel proliferation (vascularity), this improved method may be performed faster and at less expense in manufacturing. Briefly, the method of the present invention includes the step of first forming a silicone elastomer laminate base and then adding a layer of silicone elastomer by dipping the mandrel and laminate base layer into a silicone rubber dispersion, thereby creating a silicone elastomer top layer with a tacky surface, applying a coating of volatilizable particles to the tacky surface, and then finish curing the surface by heating it at an elevated temperature for a prescribed time period which also volatilizes the particles. Thus, the particles decompose and volatilize into constituent gases which interact with the layer of silicone elastomer as it is being cured to dramatically increase the "roughing" of the surface. The volatilizing during the curing step can be likened to a "boiling" action which is much more active than merely dissolving the particles in a solvent as in the prior art. Furthermore, particles which are completely covered with the silicone elastomer layer will still volatilize and force their way to the surface. Thus, the depth of the texturing achieved can be much greater than in the prior art method.

While the principal advantages and features of the present invention have been described above, a more complete and thorough understanding of the invention may be attained by referring to the drawings and description of the preferred embodiment which follow.

DETAILED DESCRIPTION OF THE PREFERRED EMBODIMENT

Figure 1:
FIG. 1 is a magnified view of the surface of a breast implant shell texturized with the method of the prior art.

As shown in FIG. 1, the method of the prior art creates a textured surface which is characterized by a number of discrete particles which are randomly arranged and some of which are deformed. Thus, while there are interstices and deformations formed in the surface, they are of limited depth and are regularly shaped.

Figure 2:
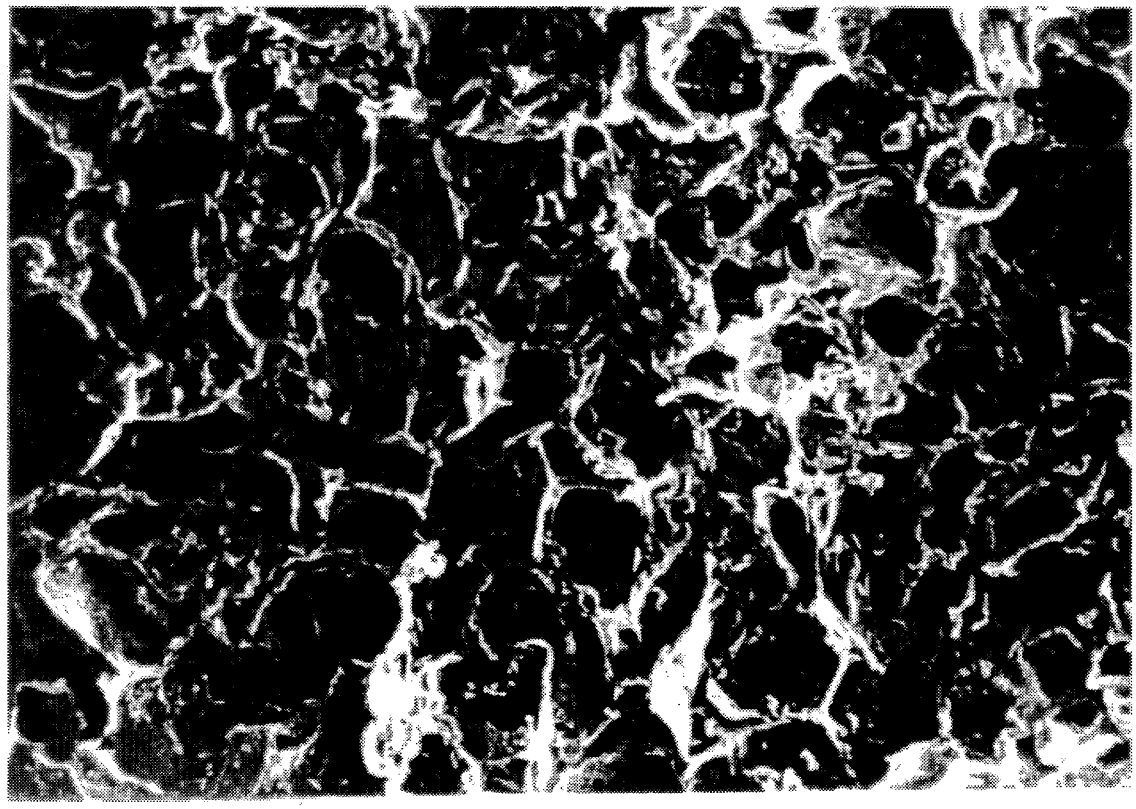
FIG. 2 is a magnified view of the surface of a breast implant texturized with the method of the present invention.

Referring to FIG. 2, a magnified view of a silicone elastomer surface which has been texturized using the method of the present invention is shown and which clearly demonstrates a textured surface having dramatically increased "roughness" as well as irregularities and depth. There is no appearance of regularity with regard to the surface and, instead, the surface gives the appearance of Swiss cheese, a sponge, or some such other surface with a large density of irregularly shaped caverns and caves extending therethrough. This dramatically roughened, textured, and porous surface provides what is believed to be a much greater opportunity for tissue ingrowth so as to dramatically improve the physiological compatibility of any implant having such a surface.

Figure 3:
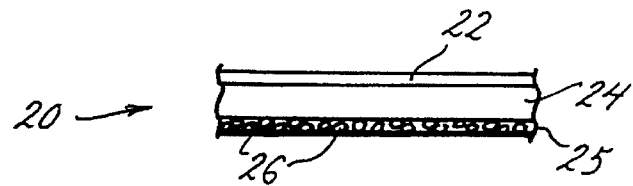
FIG. 3 is an enlarged cross-sectional view of the shell of the present invention having the discrete particles coated thereon.

As and for their preferred embodiment, the inventors have chosen a laminate structure for the silicone elastomer surface. This laminate structure is typically used in forming a shell for a breast implant. However, the laminate surface, or other silicone elastomeric surface may be used to coat any medical device desired to be surgically implanted in order to increase its physiological compatibility. Such devices might include pacemakers, for example. As shown in FIG. 3, the laminate structure 20 includes a fluorosilicone barrier layer 22 which may be approximately 0.002 inches thick, and a polydimethylsiloxane base layer 24 approximately 0.012 inches thick. This base layer 24 may be partially cross-linked for structural integrity by curing at 150° C. for approximately 30 minutes. This creates a solid, consistent base layer 24 for the subsequent texturing process thereby minimizing the possibility of potentially thin or weak spots in the finished, texturized shell.

Figure 4:
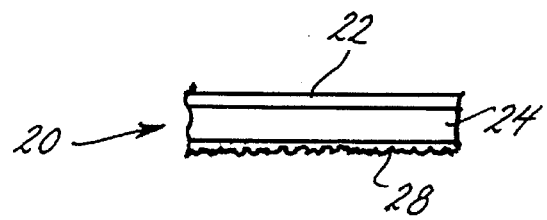
FIG. 4 is an enlarged cross-sectional view of the shell for a breast implant which has been texturized using the method of the present invention.
Figure 5:
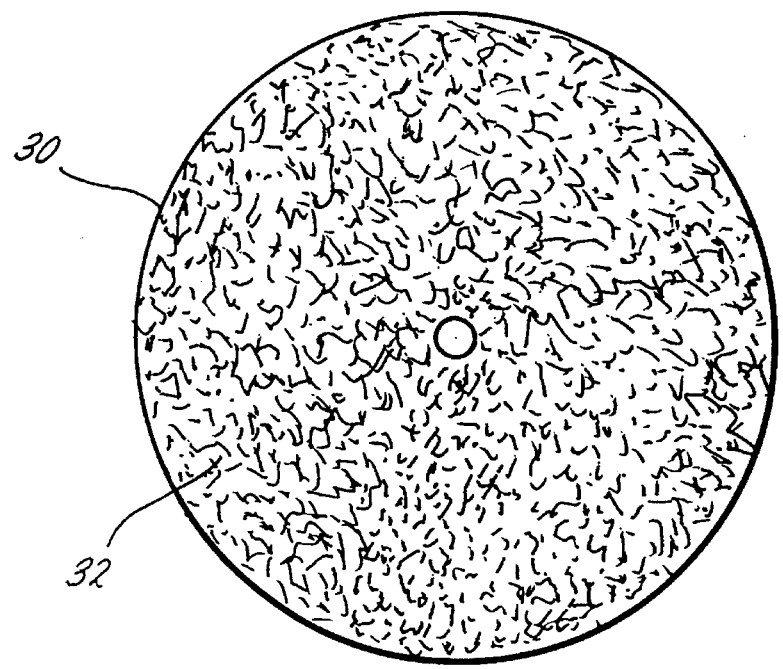
FIG. 5 is a top view of a shell for a breast implant texturized using the method of the present invention.

The texturing process begins with the smooth shell laminate 20 as the laminate remains on a mandrel (not shown) as is well known in the art for manufacturing breast implant shells. The laminate 20 and mandrel is then dipped into a polydimethylsiloxane dispersion comprised of the polydimethylsiloxane along with a solvent. The shell and mandrel are then removed to drain the excess dispersion and to permit any excess solvent to volatilize or evaporate therefrom. After evaporation, the resulting laminate 20 has a thin top layer or tacky surface 25. This tacky surface 25 is then liberally coated with ammonium carbonate particles 26 in the size range of about 350 to about 800 microns in diameter. The coated mandrel/shell is then heated for final curing at a temperature of about 150° C. for about 120 minutes. As ammonium carbonate decomposes at a temperature of about 60° C., the solid particles decompose into their constituent gases and volatilize from within the tacky surface 25 in a "boiling" action. As shown in FIG. 4, this volatilization as the laminate 20 is cured creates a highly texturized surface 28 and as depicted in greater detail in FIG. 2 is dramatically less regular to create a truly open cell structure. After the curing step, the textured surface 28 has been formed and there are no additional steps required as in the prior art such as dipping the surface into a solvent. A finished breast implant shell 30 is shown in FIG. 5 which includes a highly texturized surface 32 which demonstrates the improved physiological compatibility of the present invention.

In prototypes formed with the method of the present invention, pore openings for breast implant shells have been formed ranging from approximately 300 to 900 microns in diameter with a pore depth ranging from approximately 250 to 900 microns. Ammonium carbonate particles which range in size from about 50 microns to about 1500 microns, with a desired target range of between about 350 to 800 microns is believed to be optimal for use in the method of the present invention.

Although ammonium carbonate has been chosen for use in the preferred embodiment, it is believed only to be necessary that the particles chosen decompose and volatilize at a temperature less than the curing temperature used for the surface being texturized. By achieving volatilization as part of the curing step, it is believed that the highly roughened, textured, surface of increased depth in the present invention is formed.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for forming a layer of silicone elastomer with an open cell structure, said method comprising the steps of:

forming a layer of silicone elastomer, said layer having a tacky surface;

applying a coating of particles to said surface; and volatilizing said particles as said layer is cured, said particles thereby producing products of volatilization which render said surface into an open cell structure as said layer is cured.

2. The method of claim 1 wherein the step of volatilizing includes the step of curing said layer by heating.

3. The method of claim 2 wherein said curing step includes the step of heating said layer at about 150° C. for about 120 minutes.

4. The method of claim 1 wherein the particles are made of ammonium carbonate.

5. The method of claim 4 wherein said particles are between about 350 microns and about 800 microns in diameter.

6. The method of claim 1 wherein the forming step includes the step of dipping a surface into a silicone elastomer dispersion.

7. The method of claim 1 wherein said layer is a laminate of at least two layers, one of said layers being a base layer and the other of said layers being a barrier layer, and the method is applied to the base layer to thereby apply an open cell structure thereto.

8. The method of claim 1 wherein said method creates open cells ranging from about 300 microns to about 900 microns in diameter and with a depth from about 250 microns to about 900 microns.

9. The method of claim 1 wherein said elastomer is a shell for an implantable prosthesis, and said method is applied to the exterior surface of said prosthesis.

10. A method for forming a layer of silicone elastomer with an open cell structure, said method comprising the steps of:

forming a layer of silicone elastomer, said layer having a tacky surface;

applying a coating of particles to said surface; and curing said layer to thereby volatilize the particles and create said open cell structure.

11. The method of claim 10 wherein the curing step includes the step of heating the layer to an elevated temperature for a period of time.

12. The method of claim 11 wherein the applying step includes the step of applying a coating of particles having a temperature of volatilization substantially less than the curing temperature of said layer of elastomer.

13. The method of claim 12 wherein the forming step includes the steps of:

forming a layer of silicone elastomer laminate comprising a barrier layer and a base layer;

cross-linking said base layer; and dipping the laminate into a silicone elastomer dispersion to thereby form an external layer with a tacky surface.

14. The method of claim 13 wherein the forming step includes the step of evaporating any excess solvent from said external layer.

15. The method of claim 14 wherein the heating step includes heating the layer to a temperature of about 150° C. for about 120 minutes.

16. A method for making an implantable prosthesis having an external layer of silicone elastomer, at least a portion of which has an open cell structure, said method comprising the steps of:

forming said layer of silicone elastomer, said layer having a tacky surface;

applying a coating of particles to said surface; and curing said layer to thereby volatilize the particles and create said open cell structure therein.

17. The method of claim 16 wherein the curing step includes the step of heating the layer to an elevated temperature for a period of time.

18. The method of claim 17 wherein the applying step includes the step of applying a coating of particles having a temperature of volatilization substantially less than the curing temperature of said layer of elastomer.

19. The method of claim 18 wherein the forming step includes the steps of:

forming a layer of silicone elastomer laminate comprising a barrier layer and a base layer;

cross-linking said base layer; and dipping the laminate into a silicone elastomer dispersion to thereby form an external layer with a tacky surface.

20. The method of claim 19 wherein the forming step includes the step of evaporating any excess solvent from said external layer.

21. The method of claim 20 wherein the heating step includes heating the layer to a temperature of about 150° C. for about 120 minutes.

22. An implantable prosthesis having an external layer of silicone elastomer, said layer of silicone elastomer having an external surface with at least a portion thereof of open cell irregularly shaped structure, said implantable prosthesis being made by the method comprising the steps of:

forming a layer of silicone elastomer, said layer having a tacky surface;

applying a coating of particles to said surface; and curing said layer to thereby volatilize the particles and create said open cell structure.

23. The implantable prosthesis of claim 22 wherein substantially the entirety of the external surface has an open cell structure.

24. The implantable prosthesis of claim 23 wherein the cells in the open cell structure have a diameter from about 300 microns to about 900 microns, and a depth from about 250 microns to about 900 microns.

25. The implantable prosthesis of claim 24 wherein said implantable prosthesis is a breast implant, said breast implant including a shell filled with a fill material, said shell having said external layer of silicone elastomer.

26. The implantable prosthesis of claim 25 wherein said shell is a laminate comprised of a fluorosilicone barrier layer approximately 0.002 inches thick and a polydimethylsiloxane base approximately 0.012 inches thick, said base layer being partially cross-linked for structural integrity, said base layer forming the exterior surface.

27. A method for forming an open cell structure in an external surface of a medically implantable prosthesis, said method comprising the steps of applying a coating of particles to said surface and volatilizing said particles as said surface is finally cured, said particles thereby producing products of volatilization so that products of said volatilization shape said surface as it cures.

* * * * *